US00PP33891P2

(12) United States Plant Patent
Carter

(10) Patent No.: US PP33,891 P2
(45) Date of Patent: Jan. 18, 2022

(54) ***SALVIA* PLANT NAMED 'HUMMINGBIRD FALLS'**

(50) Latin Name: ***Salvia* x *guaranitica***
Varietal Denomination: Hummingbird Falls

(71) Applicant: Kermit E. Carter, Elk, CA (US)

(72) Inventor: Kermit E. Carter, Elk, CA (US)

( * ) Notice: Subject to any disclaimer, the term of this patent is extended or adjusted under 35 U.S.C. 154(b) by 0 days.

(21) Appl. No.: 17/351,574

(22) Filed: Jun. 18, 2021

(51) Int. Cl.
*A01H 6/50* (2018.01)
*A01H 5/02* (2018.01)

(52) U.S. Cl.
USPC ..... Plt./475

(58) Field of Classification Search
USPC ..... Plt./475
See application file for complete search history.

*Primary Examiner* — Annette H Para
(74) *Attorney, Agent, or Firm* — Weatherly IP Solutions, LLC; James M. Weatherly

(57) ABSTRACT

A new cultivar of *Salvia* named 'Hummingbird Falls' that is distinguishable by pendulous growth habit, small deep green leaves, flowers which are intense deep-purple in color and whose black calyces persist after flowering is finished.

2 Drawing Sheets

Genus and species: *Salvia* x *guaranitica*.
Variety denomination: 'Hummingbird Falls'.

BACKGROUND

The present disclosure relates to a new and distinct cultivar of *Salvia* plant, also known as a sage, a perennial that is grown for use as an ornamental landscape and container plant. The new variety is known botanically as *Salvia* x *guaranitica* and will be referred to hereinafter by the cultivar name 'Hummingbird Falls'.

'Hummingbird Falls' was selected in April 2018 from a population of seedlings which the inventor had raised from seed resulting from the controlled pollination of parent plants which the inventor had chosen for their useful characteristics. Both parents were unnamed and unreleased seedlings of *Salvia* x *guaranitica* previously raised by the inventor. The female parent was chosen for its compact growth habit. The male parent was chosen for its deep blue flowers and its dark green foliage. The hybridization was carried out by the inventor at the inventor's nursery in Elk, Calif.

'Hummingbird Falls' was selected by the inventor for its exceptionally compact and pendulous growth habit, small leaves and profuse branching and flowering—all of which allows for production and sale in hanging baskets, a novel use for the genus.

'Hummingbird Falls' was first asexually propagated in the fall of 2018 in a greenhouse at the inventor's nursery in Elk, Calif. using softwood tip cuttings. The inventor has determined during successive cycles of asexual propagation that 'Hummingbird Falls' is stable and reproduces true to type.

SUMMARY

The following traits have been repeatedly observed and represent the distinguishing characteristics of 'Hummingbird Falls'. 'Hummingbird Falls' has not been tested under all possible conditions and phenotypic differences may be observed with variations in environmental, climatic, and cultural conditions, without however, any variance in genotype.

1. 'Hummingbird Falls' exhibits a compact plant habit with profuse branching.
2. The stems of 'Hummingbird Falls' are thin in comparison with the species, such that the stems arch as they grow longer and under the weight of their terminal inflorescences.
3. The flowers of 'Hummingbird Falls' are vibrant violet-blue in color.
4. 'Hummingbird Falls' grows and flowers rapidly. Flowering plants may be produced in 10 to 12 weeks from a cutting. A flowering hanging basket may be produced in three months from planting a 3 month old starter plant.
5. The calyces of the flowers of 'Hummingbird Falls' range in color from very dark purple to black. The calyces are black in conditions of full sunlight.
6. The calyces (sepals) of 'Hummingbird Falls' persist after flowering has finished. The once-flowering inflorescences continue to display attractive and contrasting black calyces.
7. 'Hummingbird Falls' produces new flowering stems continuously from spring to fall.
8. The leaves of 'Hummingbird Falls' are small and dark green in color at all stages of growth.

DESCRIPTION OF THE PHOTOGRAPHS

The accompanying color photographs illustrate the overall appearance of the new *Salvia* cultivar 'Hummingbird Falls' showing the colors as true as it is reasonably possible to obtain in colored reproductions of this type. The photographs were taken in late May 2021 from a plant which was six months old and which had been grown for three months as a hanging basket out of doors in Santa Barbara, Calif. The plants had received one pinch after initial establishment. Colors in the photographs may differ from the color values cited in the detailed botanical description, which more accurately describes the actual colors of the new variety 'Hummingbird Falls'.

DESCRIPTION OF THE NEW VARIETY

Figure 1:
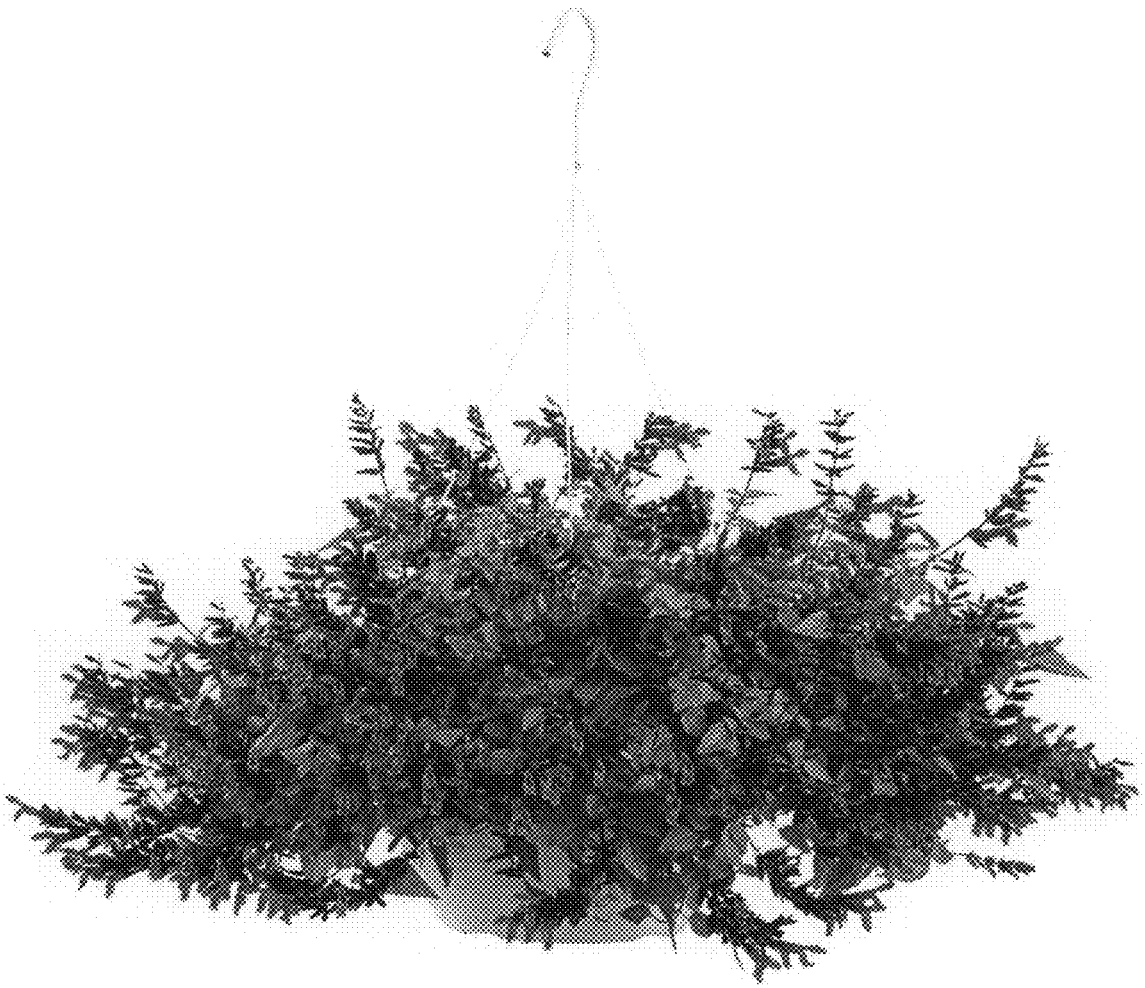
FIG. 1 depicts an entire plant of 'Hummingbird Falls'.
Figure 2:
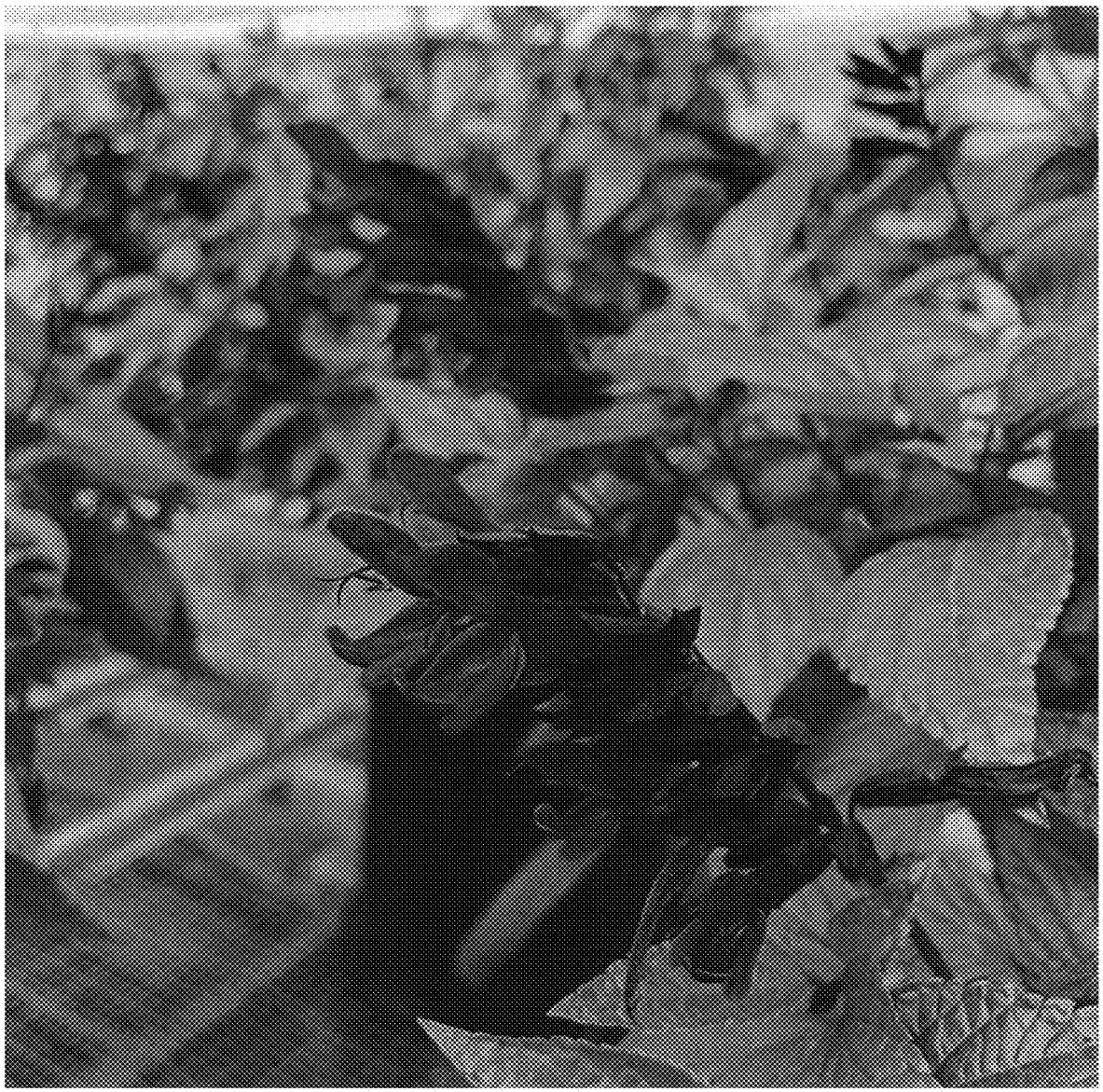
FIG. 2 depicts a close-up view of the inflorescence of 'Hummingbird Falls'.

The following detailed descriptions set forth the distinctive characteristics of 'Hummingbird Falls'. Observations, measurements, values, and comparisons were collected in June 2021 in Santa Barbara, Calif. from a six months old plant grown outdoors in full sun in a 2.5 gallon hanging basket container. Color determinations have been made in accordance with The 2007 Royal Horticultural Society Colour Chart from London England, except where general color terms of ordinary dictionary significance are used.

Classification:

*Family*.—Lamiaceae.

*Genus*.—*Salvia*.

*Species*.—X *guaranitica*.

*Common name*.—Sage.

Parentage:

*Female parent*.—*Salvia* x *guaranitica* (proprietary unnamed and unreleased seedling).

*Male parent*.—*Salvia* x *guaranitica* (proprietary unnamed and unreleased seedling).

Plant:

*Propagation method*.—Softwood tip cuttings.

*Rooting system*.—Fine and fibrous.

*Vigor*.—Moderate vigor.

*Time to develop roots*.—5 days are needed for a cutting to develop roots at recommended rooting temperature of 20° to 22° Centigrade.

*Crop time*.—Approximately 3 months are required to produce a budded and flowering plant in a quart container from a rooted cutting, and a further three months to produce a fully-flowering hanging basket from planting a quart container into a hanging basket container.

*Suggested container size*.—1 gallon container or larger for hanging basket production.

*Use*.—Ornamental for use as a container plant and as a plant for hanging baskets

*Type*.—Perennial.

*Overall dimensions* (*including inflorescences*).—After one year's growth in a 2.5 gallon container: 30 cm in height, and 50-60 cm in spread.

*Cultural requirements*.—Grow in full sun with moderate water and well-draining soil.

*Hardiness*.—USDA Zone 7.

*Form*.—Bush.

*Growth habit*.—Compact structure with stems which become pendulous with age and when flowering.

*Blooming season*.—From one month after breaking spring dormancy to first frost.

*Lastingness of blooms*.—Inflorescence has some flower for 14 days, individual flowers last for 2 to 3 days.

Stem:

*Length*.—25 cm to the base of the terminal inflorescence.

*Width*.—2 mm to 4 mm.

*Color*.—Olive green 144A towards base, becoming very dark purple N186B towards apex.

*Shape*.—Square, edges rounded.

*Texture*.—Suffruticose.

Branches:

*Quantity*.—Numerous, 50-60 branches.

*Length* (*to base of raceme*).—18 cm to 25 cm.

*Width*.—2 mm-4 mm.

*Internode length*.—4.0 cm to 5.5 cm.

*Color*.—Olive green 144A towards base, becoming very dark purple N186B towards apex.

*Shape*.—Square, edges rounded.

*Texture*.—Suffruticose.

Leaves:

*Type, arrangement*.—Simple, opposite.

*Attachment*.—Petiolate.

*Quantity per branch*.—6 to 8 pairs.

*Shape*.—Deltoid.

*Length*.—Largest leaves 7 cm., leaves typically 5.5 cm-6.0 cm.

*Width*.—Largest leaves 5.5 cm., leaves typically 3.5 cm-4.0 cm.

*Margin*.—Dentate, teeth 3 mm to 4 mm apart, 1.5 mm to 2 mm in depth.

*Thickness*.—Moderately coarse and stiff.

*Venation*.—Pinnate. Veins (adaxial surface): Depressed, color as leaf except midrib on fully expanded leaves: midrib color ranges between 138B and N186B. Veins (abaxial surface): Prominently raised, color 138B.

*Texture* (*adaxial surfaces*).—Smooth, glossy.

*Texture* (*abaxial surface*).—Matte, lightly puberulent.

*Color*.—Adaxial surface: Ranges between 141B and 143B. Abaxial surface: 138B.

*Apex*.—Acute.

*Base*.—Hastate.

*Fragrance*.—Pleasant sage fragrance when rubbed.

*Stipules*.—Present in pairs at each leaf axil. Small, petiolate (petioles 4 mm in length, 1 mm in width), shape lanceolate, 4 mm in length, 3 mm in width. All other characteristics as leaves except color lighter, 144B.

Petiole:

*Shape*.—Terete, adaxial channel.

*Length*.—4.5 cm-7.5 cm (oldest leaves).

*Width*.—2 mm.

*Texture*.—Puberulent.

*Color*.—144A except surfaces exposed to direct sun become N186B.

Peduncle:

*Length* (*to lowest flower whorl*).—4 cm to 4.5 cm.

*Shape*.—Square.

*Width*.—2 mm to 4 mm.

*Texture*.—Puberulent.

*Color*.—147A as inflorescence first forms, becoming N186B when inflorescence fully developed.

Inflorescence:

*Type*.—Terminal raceme.

*Length*.—6.5 cm to 10 cm.

*Diameter*.—3 cm.

*Flower arrangement*.—Flowers are arranged in whorls.

*Quantity of flowers*.—A range of 4 to 6 flowers per whorl and up to 7 whorls per raceme.

*Distance between whorls*.—1.5 cm-2.0 cm between lowest two whorls, decreasing to 5 mm between uppermost whorls.

*Flowering season*.—Year-round in Southern California and spring to summer elsewhere.

*Lastingness of the flowers* (*on the plant*).—From 8 days in spring to 3 days in summer.

Pedicel:

*Length*.—3 mm-4 mm.

*Width*.—0.75 mm-1.0 mm.

*Texture*.—Puberulent.

*Color*.—203A.

Calyx:

*Shape*.—Campanulate, flared toward the apex.

*Length*.—16 mm to 18 mm.

*Width*.—5 mm.

Sepals:

*Quantity*.—2, one upper, one lower, substantially longitudinally fused.

*Length*.—12 mm to 18 mm. of which 3 mm to 4 mm free.

*Width*.—7 mm when flattened.

*Shape*.—Boat shaped.

*Apex*.—Acuminate.

*Base*.—Truncate.

*Margin*.—Entire.

*Texture*.—Adaxial surface: Puberulent, longitudinally ribbed. Ribs 1 mm apart, raised less than 0.1 mm. Abaxial surface: Glabrous, longitudinal depressions.

*Color*.—203A.

Flowers:

*Quantity*.—From 4 to 6 flowers per whorl and up to 7 whorls per flowering stem.

*Shape*.—Tubular, two-lipped.

*Length* (*including corolla tube*).—4.0 cm.

*Width*.—6 mm.

*Height* (*across extremities of upper and lower lip*).—1.5 cm.

*Fragrance*.—Faint sage fragrance.

Bud (as emerges from calyx):

*Shape*.—Ellipsoidal.

*Length*.—4 mm to 5 mm.

*Width*.—3 mm to 4 mm.

*Texture*.—Pubescent, especially apex which already bears cluster of hairs on future upper petal lip.

*Color*.—86A.

Corolla:

*Shape*.—Tubular.

*Length*.—7 mm.

*Width*.—3 mm.

*Texture*.—Glabrous.

*Color* (*both surfaces*).—NN155D.

Petals:

*Quantity*.—2.

*Arrangement*.—One upper petal appearing as a hood, and one lower petal which appears as a large prominent lip.

*Upper petal*.—Aspect: Horizontal to slightly elevated. Shape: Hood. Length: 4.0 cm (including corolla tube). Width: 6 mm. Texture: Adaxial surface: Corolla tube glabrous, hood puberulent, hairs 0.5 mm. in length, color 86A. Abaxial surface: Glabrous, with two longitudinal ribs. Apex: Rounded. Base: Truncate with lower lip at corolla mouth. Margin: Smooth, entire. Color (adaxial surface) 86A, (abaxial surface): 86C.

*Lower petal, lip*.—Aspect: Downward, between 30° and 45° below horizontal. Shape: Rhomboid, concave. Length: 12 mm (free of upper petal). Width: 6 mm to 7 mm. Texture (both surfaces): Smooth, glabrous. Apex: Emarginate, depth of notch 0.5 mm. Base: Truncate. Margin: Gently undulating. Color (both surfaces): 86A-86C.

Reproductive organs:

*Stamens*.—Quantity: 2, connected to corolla tube wall, fused at base. Filament: Length: 3 cm of which 8 mm exserted from flower (upper lip) apex. Color: NN155D, except 86C where exserted. Anther: Shape: Narrowly elliptical, dorsifixed off-center. Length: 4 mm. Width: 0.5 mm to 1.0 mm. Color: 86C. Pollen: Amount: None present.

*Pistil*.—Quantity: 1. Stigma: Shape: Forked. Length: 1.5 mm-2.0 mm, gently recurved. Width: less than 0.5 mm. Color: 86C. Style: Length: 6 mm. Color: 85D.

*Ovary* (*only observed unfertilized*).—Length: 2.5 mm. Width: 1.5 mm. Color: 1B.

*Seed*.—None present.

Disease and pest susceptibility: Susceptible to sucking insects when stressed. Generally outgrows most bacterial and viral infections. Resistant to deer and rabbit grazing.

Drought tolerance: Drought tolerant.

COMPARISON WITH PARENTAL LINES AND KNOWN VARIETY

'Hummingbird Falls' is distinguishable from each of its parents and from all other varieties of *Salvia* x *guaranitica* known to the inventor by its pendulous habit and small leaves. by the color and texture of its foliage which is deeper green and thicker than either parent and by the larger size and quantity and the deeper and more intense color of its flowers.

The variety of *Salvia* x *guaranitica* which the inventor considers to be most similar to 'Hummingbird Falls' is the inventor's variety of *Salvia* plant named 'Rhythm & Blues' (U.S. Plant Pat. No. 29,585). Whereas 'Rhythm and Blues' exhibits similar violet-blue flower colors and dark green foliage, the growth habit is strongly upright, with leaves which are approximately 50% larger and whose calyces fall away after flowering. In comparison with 'Rhythm & Blues', 'Hummingbird Falls' exhibits a pendulous plant habit, with smaller foliage and which continues to hold its black calyces after flowering is finished.

I claim:

1. A new and distinct cultivar of *Salvia* plant named 'Hummingbird Falls' as described and illustrated herein.

* * * * *